(12) United States Patent
Hagedorn et al.

(10) Patent No.: US 8,865,131 B2
(45) Date of Patent: Oct. 21, 2014

(54) PREPARATION FOR USE IN OPTHALMOLOGY AND RETINAL SURGERY

(71) Applicant: Fluoron GmbH, Ulm (DE)

(72) Inventors: Nadine Hagedorn, Blaustein (DE); Stanislao Rizzo, Lucca (IT); Eduardo Rodrigues, Florianopolis (BR)

(73) Assignee: Fluoron GmbH, Ulm (DE)

( * ) Notice: Subject to any disclaimer, the term of this patent is extended or adjusted under 35 U.S.C. 154(b) by 0 days.

(21) Appl. No.: 13/689,247

(22) Filed: Nov. 29, 2012

(65) Prior Publication Data

US 2013/0084250 A1    Apr. 4, 2013

Related U.S. Application Data

(63) Continuation of application No. PCT/EP2011/002748, filed on Jun. 3, 2011.

(30) Foreign Application Priority Data

Jun. 2, 2010 (DE) .................. 10 2010 022 567

(51) Int. Cl.
   A61K 9/48    (2006.01)
   C09B 67/40   (2006.01)
   A61K 47/14   (2006.01)
   A61K 49/00   (2006.01)
   A61K 47/06   (2006.01)
   A61K 47/18   (2006.01)
   A61K 9/00    (2006.01)

(52) U.S. Cl.
   CPC ............ A61K 47/14 (2013.01); C09B 67/0082 (2013.01); A61K 49/0021 (2013.01); A61K 47/06 (2013.01); A61K 47/18 (2013.01); A61K 9/0048 (2013.01)
   USPC ..................................... 424/10.32

(58) Field of Classification Search
   USPC ..................... 424/10, 320; 514/743
   See application file for complete search history.

(56) References Cited

U.S. PATENT DOCUMENTS

| | | | |
|---|---|---|---|
| 6,211,248 B1 | 4/2001 | Menz | |
| 6,262,126 B1 | 7/2001 | Meinert | |
| 2002/0128527 A1 | 9/2002 | Meinert | |
| 2004/0092861 A1* | 5/2004 | Quiroz-Mercado | 604/22 |

FOREIGN PATENT DOCUMENTS

| | | |
|---|---|---|
| DE | 19536504 | 4/1997 |
| WO | 03-079927 | 10/2003 |

OTHER PUBLICATIONS

Heimann et al., Title: Heavytamponade 1: a review of indications, use, and complications. Eye, vol. 22, pp. 1342-1359, 2008).*
Wettetqvist et al.; Title: Tamponade efficiency of perfluorohaxyloctane and silicone oil solutions in a model eye chamber. Br. J. Ophthalmol. vol. 88, pp. 692-696, 2004).*
Bottoni et al.; Title: Perfluorcarbone liquids as postoperaative short-term vitreous substitutes in complicated retinal detachment. Graefe's Arch Clin Exp Ophthalmol. vol. 231, pp. 619-628, 1993.*
English Translation of International Search Report, PCT/EP2011/002748.
Database WPI, Week 200456, Thomson Scientific, AN 2004/577935, ZP002667540, Jul. 10, 2004, Abstract.

* cited by examiner

Primary Examiner — Johann R. Richter
Assistant Examiner — Yanzhi Zhang
(74) Attorney, Agent, or Firm — Kagan Binder, PLLC

(57) ABSTRACT

The invention relates to a dye-containing preparation for use in ophthalmology and retinal surgery.

19 Claims, No Drawings

PREPARATION FOR USE IN OPTHALMOLOGY AND RETINAL SURGERY

CROSS REFERENCES TO RELATED APPLICATIONS

This application is being filed under 35 U.S.C. 111(a) and is a continuation application of International Application No. PCT/EP2011/002748, with an international filing date of Jun. 3, 2011, which claims priority to DE 10 2010 022 567.3, with a filing date of Jun. 2, 2010, the disclosures of which are incorporated herein by reference.

FIELD OF THE INVENTION

The invention relates to a dye-containing preparation for use in ophthalmology and retinal surgery.

BACKGROUND OF THE INVENTION

The eye of vertebrates is an important and sensitive organ. If its functionality has been restricted, or if it is lacking entirely, animals in the wild are often no longer able to survive. In the vertebrate constituted by man, even though impairment of the faculty of vision is no longer a matter of life or death, having healthy eyes is nevertheless a major factor as regards quality of life and independence. Because of this, eye operations preserving the faculty of vision are becoming increasingly important.

The options for treating diseases of the eye, in particular of the retina, such as, for example, retinal detachment or retinal alteration, have increased greatly in recent years. Part of a treatment of such a type is, in the main, the surgical removal of the vitreous body (vitrectomy). For the purpose of removing the vitreous body, in the sclera of the eye three small incisions are made which extend into the posterior chamber of the eye, in which the vitreous body is located. Appropriate surgical instruments can then be introduced into the interior of the eye through the incisions. During the procedure the surgical field is, as a rule, irrigated with saline solution, since the latter is compatible with the water of the vitreous body, so an exchange of the two fluids can take place without any problems. In order that the eye does not lose its shape by reason of the loss of pressure in the course of siphoning off the stability-creating vitreous body, and does not suffer secondary injury, in place of the vitreous body a replacement fluid, which keeps the internal pressure constant, is introduced into the cavity. All the interoperative means employed in the interior of the eye, such as infusion solutions, irrigating solutions and interoperative solutions that are introduced into the eye for the purpose of stabilising the retina and preventing the curvature and detachment thereof, must be physiologically compatible, capable of being introduced well, and of being easily removed.

WO 03/079927 proposes the use of perfluorinated alkanes as exchange fluid and tamponade preparation in the course of surgical procedures in respect of the eye, in particular for surgical procedures in respect of the retina. Perfluorinated alkanes have the advantage, by reason of their high density which, in the main, lies within a range from 1.8 g/cm$^3$ to 2.0 g/cm$^3$, of collecting especially in the lower part of the vitreous body, and consequently of facilitating the treatment for the surgeon in respect of the retina. In this connection they fill up the vitreous chamber, starting from the posterior retina. Perfluorinated alkanes are distinguished by a pronounced hydrophobicity and lipophobicity—that is to say, they are neither oil-soluble nor water-soluble and therefore also do not mix with blood or body fluids, so they retain their high transparency and always allow the site of the operation to appear unclouded for the operating surgeon. Likewise, the perfluoroalkanes are not absorbed by the body and furthermore are also not metabolised. No enzyme system that is present in the human or animal body is capable of breaking down and decomposing perfluorinated alkanes. Perfluoroalkanes are therefore preferred interoperative fluids.

As a rule, the treatment of complicated retinal detachments takes the following form. After partial or complete vitrectomy has taken place, the retina is re-created by means of heavy liquids, i.e. perfluorocarbons or perfluoroalkanes, such as, for example, perfluorooctane or perfluorodecaline. By reason of the low viscosity, instilling may be effected directly above the optic disc with standard cannulas from 20 G to 23 G. By virtue of their high density, perfluorocarbons sink down onto the posterior retina and slowly fill up the vitreous chamber from the bottom. This high density makes the perfluorocarbons outstanding intraoperative instruments for the pending manipulations of the retina. After the surgical procedure and the stabilisation of the retina, perfluorooctane or perfluorodecaline is siphoned out of the vitreous chamber and replaced with traditional gas endotamponades or liquid endotamponades. In order not to jeopardise the success of the surgical procedure, it is therefore important to remove the interoperative fluids, such as the perfluoroalkanes, completely from the vitreous chamber after surgery has taken place. If thin films or small droplets of perfluorinated alkane are left behind on the retina, this can result in unwelcome side-effects such as inflammatory reactions or secondary visual handicaps. By reason of the high transparency of the perfluoroalkanes, a complete removal of the same from the site of the operation is often difficult. In addition, by reason of the good miscibility it is possible to adjust the colouring of the preparation individually for each individual case.

The object is therefore to provide a preparation for use in ophthalmology, particularly in retinal surgery, that facilitates the surgical procedure and prevents secondary injury. Furthermore, the object is to provide a preparation that is safe in its application, can be employed in targeted manner and further entails the advantage that it can be visualised without clouding the view of the field of the operation, so that a check for its presence or absence can be carried out easily.

The object is achieved by a preparation as defined in Claim 1. The dependent claims contain advantageous further developments.

Surprisingly, it has been found that a preparation that contains at least one perfluorinated alkane, at least one semifluorinated alkane and at least one dye dissolved in the semifluorinated alkane, the semifluorinated alkane having been selected from compounds of the following formula

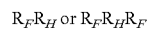

wherein $R_F$ is a linear or branched perfluoroalkyl group having 3 to 20 carbon atoms and $R_H$ is a linear or branched, saturated alkyl group having 1 to 20 carbon atoms, wherein the carbon chain exhibits a total of 4 to 30, preferably 8 to 20, carbon atoms and wherein the ratio of the perfluorinated alkane to the semifluorinated alkane amounts to 95:5 to 5:95, is optimally suitable as interoperative fluid.

The preparation according to the invention can be produced easily without great technical effort, all its components being readily obtainable. The preparation is distinguished by a high physiological compatibility and a low irritation potential, and has a sufficiently low toxicity that it can be employed without reservations in the sensitive interior of the eye. By reason of the high structural compatibility of perfluoroalkane and semifluoroalkane, mixtures can be produced over wide ranges from these two components, said mixtures being distinguished by homogeneity and monophase nature. In this connection, both the perfluoroalkane and the semifluoroalkane may, in turn, each be a mixture of perfluoroalkanes or semifluoroalkanes, respectively. The transparency of the preparation is not adversely impaired, since perfluoroalkanes and semifluorinated alkanes can be mixed homogeneously with one another in any ratio and the mixture of the preparation is monophase and transparent and, surprisingly, remains transparent even in the case of addition of a dye according to the invention.

Furthermore, by virtue of the combination, according to the invention, of perfluorinated alkane with semifluorinated alkane the density of the preparation can be optimally adjusted. This is essential, since the density of some perfluoroalkanes is regarded as too high, and in the case of their use too much pressure is exerted on the retina, which may then suffer injury. A high density of the preparation—that is to say, a density of more than 1.33 g/cm$^3$, preferentially more than 1.5 g/cm$^3$, and in particular of more than 1.7 g/cm$^3$—is preferred in accordance with the invention, since this guarantees a rapid falling of the preparation onto the retina, and accelerates the stabilisation and hence the surgical procedure. On the other hand, a density within this range is also not so high that the retina is injured by excessive pressure. The density of the solutions can be ascertained at room temperature (20-25° C.), for example by means of an oscillating-body method.

By reason of their physical properties, perfluorinated alkanes cannot be coloured directly; therefore, in accordance with the invention, a preparation is provided that permits a colouring of the perfluoroalkanes by at least one perfluorinated alkane being combined with at least one semifluorinated alkane and with a dye dissolved therein. A coloured, monophase solution is formed. This is to be ascribed both to the solubility of the colour-giving substance in the semifluorinated alkane and to the solubility of the semifluorinated alkane in the perfluoroalkane, and is essential for the preparation according to the invention.

The colouring of the preparation is important, in order to be able to check, in the course of flushing out said interoperative preparation, whether all remnants of the preparation have been completely washed out. Remnants left behind could, on the other hand, result in irritations or inflammations and, in serious cases, retinal detachment. Hence by reason of its physical properties—and in particular its chemical, physiological and biological inertness and its density—the preparation according to the invention enables an optimal stabilisation of the retina before, during and after the surgical procedure in the interior of the eye—that is to say, in particular, prior to introduction of the vitreous-body tamponade. At the same time, it enables a residue-free removal of the same from the interior of the eye, by virtue of which secondary injury after the operation can be obviated or prevented. Since the components contained in the preparation according to the invention have a high chemical as well as physical stability, the preparation can also be sterilised well, this being important in order not to cause injury to the interior of the eye by germs.

By an 'interoperative preparation' in the sense of the invention, a fluid is understood that serves for stabilisation of the retina before, during or after a surgical procedure—that is to say, for example, after siphoning off the vitreous body for the purpose of preventing the curvature or the complete detachment of the retina prior to introduction of the vitreous-body tamponade into the vitreous chamber of the eye.

Semifluorinated alkanes are known in ophthalmology and are described, for example, in EP 0 859 751, the content of which is to be referred to here expressly. By the term 'semifluorinated alkanes', generally compounds are understood that exhibit a block of a saturated linear or branched alkane and one or two blocks of a perfluorinated alkane. The semifluorinated alkanes that are used in accordance with the invention consequently exhibit a block-like structure in which blocks of perfluorinated alkyl residues are present in the vicinity of non-fluorinated saturated alkyl groups. The linear semifluorinated alkanes therefore have the following diblock structure or triblock structure:

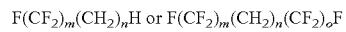

$F(CF_2)_m(CH_2)_nH$ or $F(CF_2)_m(CH_2)_n(CF_2)_oF$ wherein m and o are each integers from 3 to 20, preferentially from 3 to 8, and n is an integer from 1 to 20, preferentially from 4 to 8, wherein the total length of the carbon chain amounts to 4 to 30, preferably 8 to 20, carbon atoms. Semifluorinated alkanes are often named in abbreviated form with the number of F-bearing and H-bearing C atoms, for example F6H6 for $C_6F_{13}C_6H_{13}$ or perfluorohexylhexane.

Branched semifluorinated alkanes may furthermore exhibit, in addition to the aforementioned structural constituents, additional FCX units in the perfluorinated moiety, and additional HCY units in the alkane moiety, wherein X is, in turn, a perfluoroalkyl residue and preferably exhibits 1 to 8, and particularly preferably 2 to 4, carbon atoms, and wherein Y is an alkyl residue with preferentially 1 to 8, and particularly preferably 2 to 4, carbon atoms. Similarly, the marginal $F_3C$ groups and $H_3C$ groups may have been replaced by $FCX_2$ or $F_2CX$ or by $HCY_2$ groups or $H_2CY$ groups, wherein X and Y exhibit a structure as already represented above. As for the linear semifluorinated alkanes, also for the branched semifluorinated alkanes it holds that the sum of carbon atoms preferentially does not exceed 20. By modifications of such a type, individual semifluorinated alkanes can be produced which can be varied, depending on the field of application. By virtue of the non-substituted alkyl moiety, the semifluorinated alkanes are distinguished by a low to medium lipophilicity—that is to say, they are capable of dissolving in suitable lipophilic solvents, or of dissolving lipophilic components in themselves. This is essential for the present invention, since only by reason of this lipophilicity is it possible to impart a colour to the preparation according to the invention by dissolving a likewise lipophilic colour-giving substance.

The semifluorinated alkanes are, in themselves, transparent liquids which are physiologically compatible, commercially available and non-toxic. Furthermore, they are distinguished by a low irritation potential. They are inert—that is to say, they do not react with body fluids and cells that are present at the site of the operation—and are also not metabolised and can therefore be employed optimally as component in interoperative fluids in retinal surgery.

Perfluorinated alkanes in the sense of the invention are saturated linear, branched or cyclic alkanes with C—F bonds. Suitable perfluoroalkanes are known to a person skilled in the art from WO 03/079927, for example, and preferentially include those having 4 to 20, and particularly preferably 4 to 12, carbon atoms, for example $C_4F_{10}$, $C_5F_{12}$, $C_6F_{14}$, $C_7F_{16}$, $C_8F_{18}$, $C_9F_{20}$, $C_{10}F_{18}$ or $C_{10}F_{22}$, $C_{11}F_{24}$ or $C_{12}F_{26}$ or mixtures thereof. Particularly preferred are perfluorodecaline and perfluorooctane. Mixtures of isomers and/or mixtures of perfluoroalkanes of differing chain length are also suitable, for example a mixture of perfluoroheptane, perfluorooctane and perfluorononane. Suitable in accordance with the invention are liquid perfluoroalkanes that exhibit a high refractive index and a high transparency and are further distinguished by a viscosity that makes them easy to introduce into the vitreous chamber and easy to remove therefrom. This is important, in order in the course of the surgical procedure to leave, as far as possible, no injury, for example to the sclera of the eye, through which the interoperative fluid is to be introduced, this being preferentially effected by means of a very thin needle of 20 to 23 gauge or even 25 gauge.

Perfluoroalkanes are employed in retinal surgery by reason of their high density and inertness. However, by reason of their pronounced hydrophobicity and lipophobicity, perfluoroalkanes cannot be mixed with other beneficial substances. A high proportion of perfluorinated alkane is required, as already explained, in order to bring the density of the preparation to a value such that the preparation falls down onto the retina completely and without considerable temporal delay and hence stabilises the retina optimally. In order to achieve this positive effect, it is necessary that the mixing ratio, relative to volume, amounts to 95:5 to 5:95 perfluoroalkane to semifluorinated alkane. The higher the proportion of perfluoroalkane, the higher the density of the overall preparation, and the more rapidly and more completely does the preparation fall onto the retina in the interior of the eye and stabilise it. The mixing ratio is accordingly chosen in such a way that the aforementioned positive properties of the overall preparation are achieved. A certain proportion of semifluorinated alkane is necessary, however, in order to provide the coloured nature of the preparation according to the invention. By simple routine experiments a person skilled in the art can find out the optimal ratio as a function of the components used.

Perfluoroalkanes and semifluorinated alkanes (SFA) mix in any ratio; therefore the selection of the compounds to be mixed in the given case is not critical, so long as they are liquid at room temperature (i.e. about 25° C.) and body temperature (i.e. about 37° C.). Preferred combinations are perfluoroalkanes having 8 or 10 carbon atoms with semifluorinated alkanes having 8 to 16 carbon atoms. Advantageous mixtures are obtained, for example, from perfluorodecaline and/or perfluorooctane with $C_4F_9C_5H_{11}$, $C_6F_{13}C_6H_{13}$ and/or $C_6F_{13}C_8H_{17}$.

The proportion of semifluorinated alkane preferentially amounts to 5 vol. % to 60 vol. %, relative to the total volume of the preparation according to the invention, preferably 7 vol. % to 50 vol. %, more preferably 10 vol. % to 40 vol. %, and particularly preferably 10 vol. % to 30 vol. %. If the proportion of semifluorinated alkane lies within the specified range, a sufficient quantity of colour-giving substance can be dissolved therein so that the preparation according to the invention exhibits overall a visually readily apparent colour intensity which can be perceived well at the site of application. As a rule, a proportion of less than 5 vol. % is not sufficient to achieve an adequate colouring. In the case of proportions of more than 60 vol. % of semifluorinated alkane, the density of the overall preparation falls to a value at which the preparation can possibly no longer adequately stabilise the retina in situ. The preparation floats in the vitreous chamber, and there is a risk that it will be simply washed out in the course of irrigating above the operating room.

A further constituent that is essential to the invention is a dye by way of colour-giving substance which dissolves in the semifluorinated alkane. By 'dyes', generally substances are understood that, in contrast to pigments, dissolve in solvents. Moreover, by 'dyes' or 'colour-giving substances' in the sense of the invention, such substances are understood which reflect light in the visible wavelength range—that is to say, from about 350 nm to 750 nm—and/or by excitation by means of energy, for example in the form of heat or light, can be excited to reflect light having a wavelength within the visible wavelength range.

Suitable for the present invention are solvent dyes and fat dyes, to the extent that they are soluble and physiologically compatible in the semifluorinated alkanes used in accordance with the invention. A substance that has an intrinsic colour in the visible spectral region of light and is soluble in aprotic, lipophilic solvents is designated as a 'solvent dye'. Said substance is distinguished, in the main, by a likewise lipophilic basic structure, and is therefore also readily soluble in the semifluorinated alkanes used in accordance with the invention. Fat-soluble and oil-soluble dyes, i.e. dyes that dissolve in lipophilic solvents, are usually designated as fat dyes. Examples of a fat dye are dyes of the Sudan class, such as, for example, Sudan I, Sudan II, Sudan III and Sudan IV.

The dye that is used in accordance with the invention may be a fluorescent dye, that is to say, a dye that after the action of energy, particularly in the form of heat or light—in general, radiation, is excited to emit light in the visible spectral range and then fluoresces. Also in the case of the fluorescent dyes a sufficient solubility in the semifluorinated alkane is essential, since otherwise no colouring of the overall preparation according to the invention can be achieved.

In accordance with the invention, such dyes enter into consideration which dissolve in semifluorinated alkanes to such an extent that the solution is visibly coloured. By 'visibly coloured' in this connection it is understood that with the naked eye it can be discerned that the solution has a colour, for example when it is viewed against a white background. By 'dissolve', it is understood that at least so much of the colour-giving substance dissolves homogeneously in the semifluorinated alkane at room temperature that a sufficient colouring of the preparation as a whole is achieved and no formation of a second phase occurs. In practice, so much colour-giving substance is dissolved in semifluorinated alkane until, after commingling with the desired quantity of perfluorinated alkane, a sufficient depth of colour of the overall preparation at the temperature at the site of the operation (as a rule, about 35° C. to 37° C.) has been achieved. Since there are no limits as regards miscibility, the ratio can be adjusted optimally in the given case, i.e. the depth of colour can be individually adapted to the application site, the operating surgeon, the lighting conditions, etc. The depth of colour can be changed by the proportion of dye that has been dissolved in the semifluorinated alkane beings varied, and/or by the proportion of coloured semifluorinated alkane in the overall preparation being varied. Any undissolved fractions of colour-giving substance must be filtered off prior to further processing of the preparation according to the invention. The depth of colour can be easily determined by means that are known to a person skilled in the art, for example by means of UV-VIS spectroscopy or other suitable photometric processes.

In principle, any dye that is soluble in the semifluorinated alkane may be used if it is non-toxic in the applied concentration and has sufficient biocompatibility, physiological as well as chemical inertness, and low irritation potential, so that the tissue is not injured during the surgical procedure. The solubility of the colour-giving substance used in accordance with the invention is so high at the temperature that prevails at the site of the operation that no formation of a second phase occurs, for instance by the colour-giving substance being precipitated out.

Use is preferably made of such a dye which in a quantity that is as low as possible still provides a visible colouring. Particularly suitable, but not limiting, examples of dyes in the sense of the invention are dyes selected from the group consisting of: Solvent Blue 36, Solvent Blue 35, Solvent Green 5, Solvent Violet 13, Solvent Blue 8, Solvent Blue 18, Solvent Blue 63, Solvent Green 3, Solvent Green 7, Solvent Violet 10, Solvent Violet 12, Solvent Violet 26, Solvent Red 27, Solvent Yellow 56, Solvent Green 3, Solvent Yellow 33, Solvent Red 19, Solvent Red 1, Solvent Yellow 16, whereby Solvent Blue 36, Solvent Blue 35, Solvent Green 5, Solvent Violet 13 and also Sudan I to IV are preferred by reason of their extremely good physiological compatibility and good dissolving properties in semifluorinated alkanes. Use may also be made of mixtures of dyes, for example if a particular hue is to be achieved. Use is preferably made of only one dye for the preparation in each instance.

The dye according to the invention is used in a quantity that dyes sufficiently. The suitable quantity in the given case depends on the dye used in the given case, and can be easily determined by a person skilled in the art with routine tests. As a rule, particularly in the case of the dyes named above as preferred, a quantity of less than 0.08 g/L suffices in order to obtain a sufficiently visible colouring of the preparation. The dye is preferably employed in a quantity from 0.08 g/L to 0.001 g/L, more preferably 0.07 g/L to 0.003 g/L, for example 0.06 g/L (=0.006%) to 0.006 g/L (=0.0006%). In this connection the specified quantities relate in each instance to the total weight of the finished preparation.

The preparation according to the invention may additionally contain, besides the components described previously, pharmaceutically active constituents such as antibiotically active substances, for example cyclosporine, glucocorticoids such as triamcinolone, dexamethasone, or active substances such as indomethacin, colchicine, heparin, and cytostatics. In addition, fat-soluble antioxidants such as lutein, zeaxanthin, vitamin E may be added to the mixture.

Production of the preparation according to the invention may be effected by the colour-giving substance being mixed homogeneously in the intended quantity of semifluorinated alkane with the aid of a suitable stirring element and subsequently by the perfluoroalkane being added. The preparation is stored overnight at room temperature in a closed vessel and is filtered prior to further processing. The preparation according to the invention can be mixed individually for each procedure. Preferably a premixed solution is provided, particularly preferably in the form of an infusion solution.

The preparation according to the invention is ideally suited for use in ophthalmology, particularly in retinal surgery, and is particularly suitable in the case of vitrectomy or for surgical procedures in connection with retinal detachment.

The invention therefore also provides the use of the preparation according to the invention in ophthalmology, in retinal surgery, in particular for vitrectomy or surgical procedures in connection with retinal detachment.

EXAMPLES

Unless otherwise stated, the quantitative data for the dye relate to parts by weight relative to the total volume of the preparation. The quantitative data for the solvents are vol. % and relate to the total volume. For the colouring, base solutions of dye were prepared which each contained a specific dye in a concentration of 0.06 g/L in semifluorinated alkane. From these base solutions, for the production of the example solutions in each instance the volume fractions specified in the Tables were then withdrawn and mixed with perfluoroalkane in the specified quantity.

Example 1

| Dye | Content of semifluorinated alkane $C_6F_{13}$—$C_8H_{17}$ | Content of perfluorinated alkane Perfluorooctane | Concentration of dye in g/L | Density [g/cm$^3$] | Colour intensity |
|---|---|---|---|---|---|
| Solvent Blue 36 | 10 vol. % | 90 vol. % | 0.006 | 1.71 | pale |
| Solvent Blue 36 | 20 vol. % | 80 vol. % | 0.012 | 1.66 | mild |
| Solvent Blue 36 | 30 vol. % | 70 vol. % | 0.018 | 1.62 | medium |
| Solvent Blue 36 | 60 vol. % | 40 vol. % | 0.036 | 1.58 | strong |

Dye

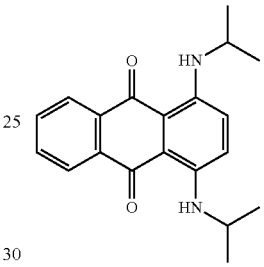

Solvent Blue 36
Formula: $C_{20}H_{22}N_2O_2$
Molecular weight: 322.41
Perfluorooctane: boiling-point: 105° C.
Vapour pressure: 18.5 mbar at 25° C.

From the semifluorinated alkane and from the dye, by mixing with a paddle stirrer a homogeneous solution was produced which was subsequently mixed homogeneously with the perfluorinated alkane. The density of the solutions was ascertained at room temperature (20° C.) by means of an oscillating-body method. In this connection, use was made of the DA-100M density meter manufactured by Mettler-Toledo.

The preparation could be easily drawn up through a syringe with a cannula of 25 gauge and drained out of it again. It was stable over a storage-period of 42 hours at 120° C., corresponding to a storage-period in ambient conditions of about 3 years and 8 months (taking the van't Hoff equation into account, a speed of reaction of one hour at 100° C. (reflux of an aqueous solution) corresponds to about 32 days at 20° C.). After this time, the solution displayed no change visually under the microscope—that is to say, neither separation nor cloudiness. Similarly, the preparation could be sterilised without substantial visually perceptible changes by sterilisation by means of sterile filter with pore size 0.2 μm.

Example 2

| Dye | Content of semifluorinated alkane $C_6F_{13}$—$C_8H_{17}$ | Content of perfluorinated alkane Perfluorodecaline | Concentration of dye in g/L | Density [g/cm$^3$] | Colour intensity |
|---|---|---|---|---|---|
| Solvent Blue 36 | 10 vol. % | 90 vol. % | 0.006 | 1.86 | pale |

-continued

| Dye | Content of semifluorinated alkane $C_6F_{13}$—$C_8H_{17}$ | Content of perfluorinated alkane Perfluorodecaline | Concentration of dye in g/L | Density [g/cm$^3$] | Colour intensity |
|---|---|---|---|---|---|
| Solvent Blue 36 | 20 vol. % | 80 vol. % | 0.012 | 1.80 | mild |
| Solvent Blue 36 | 30 vol. % | 70 vol. % | 0.018 | 1.73 | medium |
| Solvent Blue 36 | 60 vol. % | 40 vol. % | 0.036 | 1.67 | strong |

Perfluorodecaline: boiling-point: 142° C.
Vapour pressure: 8 mbar at 25° C.

The stated components were formulated as in Example 1 into a transparent coloured preparation. The density was determined as in Example 1.

The preparation could be drawn up through a syringe with a cannula of 25 gauge and drained out of it again. It was stable over a storage-period of 42 hours at 120° C. After this time, the solution displayed no change visually under the microscope—that is to say, neither separation nor cloudiness. The preparation was sterilised for 5 hours by means of dry heat at a temperature of 135° C., whereby it did not change in visually perceptible manner.

Example 3

| Dye | Content of semifluorinated alkane $C_6F_{13}$—$C_8H_{17}$ | Content of perfluorinated alkane Perfluorooctane | Concentration of dye in g/L | Density [g/cm$^3$] | Colour intensity |
|---|---|---|---|---|---|
| Solvent Blue 35 | 10 vol. % | 90 vol. % | 0.006 | 1.71 | pale |
| Solvent Blue 35 | 20 vol. % | 80 vol. % | 0.012 | 1.66 | mild |
| Solvent Blue 35 | 30 vol. % | 70 vol. % | 0.018 | 1.62 | medium |
| Solvent Blue 35 | 60 vol. % | 40 vol. % | 0.036 | 1.58 | strong |

Dye
Solvent Blue 35

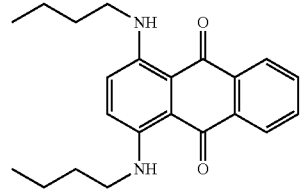 [SMILES: CCCCNc1ccc(NCCCC)c2c1C(=O)c1ccccc1C2=O]

From the semifluorinated alkane and from the dye, by mixing with a paddle stirrer a homogeneous solution was produced which was subsequently mixed homogeneously with the perfluorinated alkane. The density of the solutions was ascertained at room temperature (20° C.) by means of an oscillating-body method. In this connection, use was made of the DA-100M density meter manufactured by Mettler-Toledo.

The preparation could be easily drawn up through a syringe with a cannula of 25 gauge and drained out of it again. It was stable over a storage-period of 42 hours at 120° C., displayed no change visually under the microscope—that is to say, neither separation nor cloudiness. Similarly, the preparation could be sterilised without substantial visually perceptible changes by sterilisation by means of sterile filter with pore size 0.2 μm.

Example 4

| Dye | Content of semifluorinated alkane $C_6F_{13}$—$C_8H_{17}$ | Content of perfluorinated alkane Perfluorodecaline | Concentration of dye in g/L | Density [g/cm$^3$] | Colour intensity |
|---|---|---|---|---|---|
| Solvent Blue 35 | 10 vol. % | 90 vol. % | 0.006 | 1.86 | pale |
| Solvent Blue 35 | 20 vol. % | 80 vol. % | 0.012 | 1.80 | mild |
| Solvent Blue 35 | 30 vol. % | 70 vol. % | 0.018 | 1.73 | medium |
| Solvent Blue 35 | 60 vol. % | 40 vol. % | 0.036 | 1.67 | strong |

The stated components were formulated as in Example 1 into a transparent coloured preparation. The density was determined as in Example 1.

The preparation could be drawn up through a syringe with a cannula of 25 gauge and drained out of it again. It was stable over a storage-period of 42 hours at 120° C. After this time, the solution displayed no change visually under the microscope—that is to say, neither separation nor cloudiness. The preparation was sterilised for 5 hours by means of dry heat at a temperature of 135° C., whereby it did not change in visually perceptible manner.

Example 5

| Dye | Content of semifluorinated alkane $C_6F_{13}$—$C_8H_{17}$ | Content of perfluorinated alkane Perfluorodecaline | Concentration of dye in g/L | Density [g/cm$^3$] | Colour intensity |
|---|---|---|---|---|---|
| Solvent Violet 13 | 10 vol. % | 90 vol. % | 0.006 | 1.71 | pale |
| Solvent Violet 13 | 20 vol. % | 80 vol. % | 0.012 | 1.66 | mild |
| Solvent Violet 13 | 30 vol. % | 70 vol. % | 0.018 | 1.62 | medium |
| Solvent Violet 13 | 60 vol. % | 40 vol. % | 0.036 | 1.58 | strong |

From the semifluorinated alkane and from the dye, by mixing with a paddle stirrer a homogeneous solution was produced which was subsequently mixed homogeneously with the perfluorinated alkane. The density of the solutions was ascertained at room temperature (20° C.) by means of an oscillating-body method. In this connection, use was made of the DA-100M density meter manufactured by Mettler-Toledo.

The preparation could be easily drawn up through a syringe with a cannula of 25 gauge and drained out of it again. It was stable over a storage-period of 42 hours at 120° C., displayed no change visually under the microscope—that is to say, neither separation nor cloudiness. Similarly, the preparation could be sterilised without substantial visually perceptible changes by sterilisation by means of sterile filter with pore size 0.2 μm.

Example 6

| Dye | Content of semifluorinated alkane $C_6F_{13}$—$C_8H_{17}$ | Content of perfluorinated alkane Perfluorodecaline | Concentration of dye in g/L | Density [g/cm$^3$] | Colour intensity |
|---|---|---|---|---|---|
| Solvent Violet 13 | 10 vol. % | 90 vol. % | 0.006 | 1.86 | pale |
| Solvent Violet 13 | 20 vol. % | 80 vol. % | 0.012 | 1.80 | mild |
| Solvent Violet 13 | 30 vol. % | 70 vol. % | 0.018 | 1.73 | medium |
| Solvent Violet 13 | 60 vol. % | 40 vol. % | 0.036 | 1.67 | strong |

From the semifluorinated alkane and from the dye, by mixing with a paddle stirrer a homogeneous solution was produced which was subsequently mixed homogeneously with the perfluorinated alkane. The density of the solutions was ascertained at room temperature (20° C.) by means of an oscillating-body method. In this connection, use was made of the DA-100M density meter manufactured by Mettler-Toledo.

The preparation could be easily drawn up through a syringe with a cannula of 25 gauge and drained out of it again. It was stable over a storage-period of 42 hours at 120° C., displayed no change visually under the microscope—that is to say, neither separation nor cloudiness. Similarly, the preparation could be sterilised without substantial visually perceptible changes by heating to 135° C. for 5 hours.

Example 7

| Dye | Content of semifluorinated alkane $C_6F_{13}$—$C_8H_{17}$ | Content of perfluorinated alkane Perfluorooctane | Density [g/cm$^3$] | Colour intensity |
|---|---|---|---|---|
| Solvent Green 5 | 30 vol. % | 70 vol. % | 1.62 | medium |
| Solvent Green 5 | 60 vol. % | 40 vol. % | 1.58 | medium |

Dye: Solvent Green 5 (Keyplast Yellow Green 7G)
diisobutyl 3,9-perylenedicarboxylate → fluorescent dye

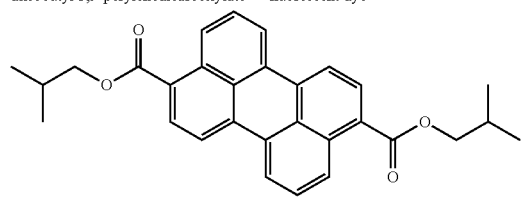

Formula: $C_{30}H_{28}O_4$
Molecular Weight: 452.54
Perfluorooctane F6H8

A preparation was produced with the fluorescing dye Solvent Green 5. To this end, the stated components were formulated as in Example 1 into a transparent coloured preparation. The density was determined as in Example 1.

The preparation could be drawn up through a syringe with a cannula of 25 gauge and drained out of it again. It was stable over a storage-period of 42 hours at 120° C. After this time the solution displayed no change visually under the microscope—that is to say, neither separation nor cloudiness. The preparation could be sterilised without substantial visually perceptible changes by sterilisation by means of sterile filter with pore size 0.2 μm.

Example 8

| Dye | Content of semifluorinated alkane $C_6F_{13}$—$C_8H_{17}$ | Content of perfluorinated alkane Perfluorooctane | Density [g/cm$^3$] | Colour intensity |
|---|---|---|---|---|
| Solvent Green 5 | 30 wt. % | 70 wt. % | 1.74 | medium |
| Solvent Green 5 | 60 wt. % | 40 wt. % | 1.68 | medium |

A preparation was produced with the fluorescing dye Solvent Green 5. To this end, the stated components were formulated as in Example 1 into a transparent coloured preparation. The density was determined as in Example 1.

The preparation could be drawn up through a syringe with a cannula of 25 gauge and drained out of it again. It was stable over a storage-period of 42 hours at 120° C. After this time the solution displayed no change visually under the microscope—that is to say, neither separation nor cloudiness. The preparation was sterilised for 5 hours by means of dry heat at a temperature of 135° C., whereby it did not change in visually perceptible manner.

Example 9

| Dye | Content of semifluorinated alkane $C_4F_9$—$C_5H_{11}$ | Content of perfluorinated alkane Perfluorodecaline | Concentration of dye in g/L | Density [g/cm$^3$] | Colour intensity |
|---|---|---|---|---|---|
| Solvent Violet 13 | 10 vol. % | 90 vol. % | 0.006 | 1.86 | pale |

A preparation was produced with the dye Solvent Violet 13. To this end, the stated components were formulated as in Example 1 into a transparent coloured preparation. The density was determined as in Example 1.

Example 10

| Dye | Content of semifluorinated alkane $C_6F_{13}$—$C_6H_{13}$ | Content of perfluorinated alkane Perfluorodecaline | Concentration of dye in g/L | Density [g/cm$^3$] | Colour intensity |
|---|---|---|---|---|---|
| Solvent Violet 13 | 10 vol. % | 90 vol. % | 0.006 | 1.87 | pale |

A preparation was produced with the dye Solvent Violet 13. To this end, the stated components were formulated as in Example 1 into a transparent coloured preparation. The density was determined as in Example 1.

The invention claimed is:

1. A preparation for use in ophthalmology or retinal surgery, containing at least one perfluorinated alkane, at least one semifluorinated alkane and at least one colour-giving substance dissolved in the semifluorinated alkane, the semifluorinated alkane being selected from:

$$R_F R_H \text{ or } R_F R_H R_F$$

wherein $R_F$ is a linear or branched perfluoroalkyl group having 3 to 20 carbon atoms and $R_H$ is a linear or branched, saturated alkyl group having 1 to 20 carbon atoms, wherein the total chain length is 4 to 30 carbon atoms.

2. The preparation according to claim 1, wherein the colour-giving substance is a solvent dye or fat dye.

3. The preparation according to claim 1, wherein the dye is a solvent dye that is selected from the group consisting of: Solvent Blue 36, Solvent Blue 35, Solvent Green 5, Solvent Violet 13, Solvent Blue 8, Solvent Blue 18, Solvent Blue 63, Solvent Green 3, Solvent Green 7, Solvent Violet 10, Solvent Violet 12, Solvent Violet 26, Solvent Red 27, Solvent Yellow 56, Solvent Green 3, Solvent Yellow 33, Solvent Red 19, Solvent Red 1, Solvent Yellow 16.

4. The preparation according to claim 1, wherein the dye is a fat dye that is selected from the group consisting of: Sudan I, Sudan II, Sudan III, Sudan IV.

5. The preparation according to claim 1, wherein the dye is selected from dye that fluoresces.

6. The preparation according to claim 1, wherein the dye is contained in a finished preparation in a quantity of from 0.08 g/L to 0.001 g/L.

7. The preparation according to claim 1, wherein the dye is contained in the finished preparation in a quantity of from 0.07 g/L to 0.003 g/L.

8. The preparation according to claim 1, wherein the dye is contained in the finished preparation in a quantity of from 0.06 g/L to 0.006 g/L.

9. The preparation according to claim 1, wherein the perfluoroalkane is selected from the group consisting of: $C_4F_{10}$, $C_5F_{12}$, $C_6F_{14}$, $C_7F_{16}$, $C_8F_{18}$, $C_9F_{20}$ and $C_{10}F_{22}$.

10. The preparation according to claim 1, wherein the preparation has a density of more than 1 g/cm$^3$.

11. The preparation according to claim 1, wherein the preparation has a density of more than 1.33 g/cm$^3$.

12. The preparation according to claim 1, wherein the preparation has a density of more than 1.5 g/cm$^3$.

13. The preparation according to claim 1, wherein the quantity of semifluorinated alkane is 5 vol. % to 60 vol. %, relative to the total volume of the preparation.

14. The preparation according to claim 1, wherein the quantity of semifluorinated alkane is 10 vol. % to 40 vol. %, relative to the total volume of the preparation.

15. The preparation according to claim 1, wherein the quantity of semifluorinated alkane is 10 vol. % to 20 vol. %, relative to the total volume of the preparation.

16. The preparation according to claim 1, in the form of an infusion fluid.

17. A method of carrying out ophthalmic surgery comprising using the preparation of claim 1 as an interoperative fluid.

18. A method of stabilizing the retina comprising infusing the preparation of claim 1 into the eye.

19. The preparation according to claim 1, wherein the ratio of the perfluorinated alkane to the semifluorinated alkane, relative to volume, amounts to 95:5 to 5:95.

* * * * *